(12) United States Patent
Harnett et al.

(10) Patent No.: US 8,143,442 B2
(45) Date of Patent: Mar. 27, 2012

(54) PREPARATION FOR A CYCLOHEXANECARBOXYLIC ACID DERIVATIVE AND INTERMEDIATES

(75) Inventors: Gerard John Harnett, Ennis (IE); Ursula Hoffmann, Muttenz (CH); Michael Jansen, Bartenheim (FR); Reinhard Reents, Muenchenstein (CH); Tim Sattelkau, Ludwigshafen (DE); Dennis A. Smith, Ennis (IE); Helmut Stahr, Loerrach (DE)

(73) Assignee: Hoffmann-LA Roche Inc., Nutley, NJ (US)

(*) Notice: Subject to any disclaimer, the term of this patent is extended or adjusted under 35 U.S.C. 154(b) by 60 days.

(21) Appl. No.: 12/414,698

(22) Filed: Mar. 31, 2009

(65) Prior Publication Data

US 2009/0253928 A1 Oct. 8, 2009

(30) Foreign Application Priority Data

Apr. 4, 2008 (EP) .................... 08154078
Jan. 22, 2009 (EP) .................... 09151065

(51) Int. Cl.
*C07C 61/08* (2006.01)
*C07C 229/40* (2006.01)
*C07C 51/60* (2006.01)
*C07C 327/16* (2006.01)
*C07C 255/46* (2006.01)
*C07C 231/00* (2006.01)

(52) U.S. Cl. ........ 562/400; 562/457; 562/859; 558/257; 558/378; 564/139

(58) Field of Classification Search ............... 558/257, 558/378; 562/400; 564/123, 124
See application file for complete search history.

(56) References Cited

U.S. PATENT DOCUMENTS

| | | | |
|---|---|---|---|
| 2,899,458 A | 8/1959 | Wilson | |
| 4,129,595 A | 12/1978 | Suzuki | |
| 4,283,420 A | 8/1981 | Pigerol et al. | |
| 4,515,960 A | 5/1985 | Teetz | |
| 7,858,823 B2 * | 12/2010 | Hoffmann et al. | 562/400 |
| 2003/0092708 A1 | 5/2003 | Shinkai et al. | |
| 2007/0100154 A1 | 5/2007 | Hoffmann et al. | |
| 2008/0154059 A1 | 6/2008 | Hoffmann et al. | |

FOREIGN PATENT DOCUMENTS

| | | |
|---|---|---|
| EP | 0094633 | 11/1983 |
| EP | 1 020 439 | 7/2000 |
| WO | WO 98/54124 | 12/1998 |
| WO | WO 2004/056752 A1 | 7/2004 |
| WO | WO 2005/003116 | 1/2005 |
| WO | WO 2007/051714 | 5/2007 |

OTHER PUBLICATIONS

Arseniyadis et al., Organic Reactions, 1984, John Wiley & Sons, Inc., 31, pp. 20 and 78.*
Shinkai et al., J. Med. Chem., 43, pp. 3566-3572 (2000).
Hauser, M., Journal of the American Chemical Society, vol. 105, pp. 5688-5690 (1983) XP002416563.
March, J. Advanced Organic Chemistry Third Ed. (1985) pp. 388-389, XP002488845.
Roth, et al., J. Med. Chem., vol. 35, No. 9, pp. 1609-1617 (1992) XP002437815.
Creger, P.L., J. Am. Chem. Soc., vol. 92, No. 5, pp. 1397-1398 (1970) XP002437816.
Creger, P.L., Ann. Rep. Med. Chem., 12, pp. 278-287 (1977).
Petragnani et al., Synthesis, pp. 521-578 (1982).
Shiner et al., J. Am. Chem. Soc., 103, pp. 436-442 (1981).
Williams et al., J. Org. Chem., 45, pp. 5082-5088 (1980).
Severin et al., Synthesis, 4, pp. 305-307 (1982).
Tavares et al., J. Med. Chem., 47, pp. 5049-5056 (2004).
Goossen et al., Adv. Synth. Catal., 345, pp. 943-947 (2003).
Fleming, F et al, Jour. of Organic Chem, 70(6) (2000).
Fauvarsue, J.-F. et al, Sciences Chimiques Serie C, 278, (1968) 1162-1165.

* cited by examiner

*Primary Examiner* — Kamal Saeed
*Assistant Examiner* — Kristin Bianchi
(74) *Attorney, Agent, or Firm* — George W. Johnston; Dennis P. Tramaloni; Brian C. Remy

(57) ABSTRACT

A process for the preparation of a compound of formula (Ia):

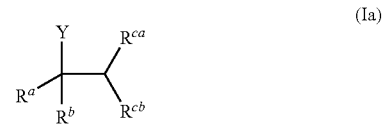

which are useful as intermediates in the preparation of i.a. pharmaceutically active compounds.

15 Claims, No Drawings

PREPARATION FOR A CYCLOHEXANECARBOXYLIC ACID DERIVATIVE AND INTERMEDIATES

PRIORITY TO RELATED APPLICATIONS

This application claims the benefit of European Patent Application No. 08154078.3, filed Apr. 4, 2008 and European Patent Application No. 09151065.1, filed Jan. 22, 2009. The entire contents of the above-identified applications are hereby incorporated by reference.

FIELD OF THE INVENTION

The present invention relates to a process for the preparation of a cyclohexanecarboxylic acid derivative which is useful as an intermediate in the preparation of pharmaceutically active compounds.

SUMMARY OF THE INVENTION

The present invention generally provides a process for the preparation of compound of formula $I_a$:

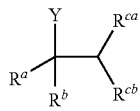

wherein, $R^a$ is hydrogen, $(C_1-C_8)$alkyl, halo-$(C_1-C_8)$alkyl, $(C_1-C_6)$alkoxy, $(C_1-C_6)$alkoxy-$(C_1-C_6)$alkylene, hetero-$(C_1-C_8)$alkyl, —$(C_3-C_6)$cycloalkyl, $(C_3-C_6)$cycloalkyl-$(C_1-C_6)$alkylene, aryl, aralkyl, heteroaryl, heteroaryl-$(C_1-C_6)$alkylene, $(C_1-C_6)$alkyl-carbonyl, aryl-carbonyl, aryl-$(C_1-C_6)$alkylene-carbonyl, heteroaryl-carbonyl, heteroaryl-$(C_1-C_6)$alkylene-carbonyl, acyl, amino; —$NO_2$, -cyano, —$SO_2OR'$, or —$PO(OR')_2$;

$R_b$ is hydrogen, $(C_1-C_8)$alkyl, halo-$(C_1-C_8)$alkyl, $(C_1-C_6)$alkoxy, $(C_1-C_6)$alkoxy-$(C_1-C_6)$alkylene, hetero-$(C_1-C_8)$alkyl, $(C_3-C_6)$cycloalkyl, $(C_3-C_6)$cycloalkyl-$(C_1-C_6)$alkylene, aryl, aralkyl, heteroaryl, heteroaryl-$(C_1-C_6)$alkylene, $(C_1-C_6)$alkyl-carbonyl, aryl-carbonyl, aryl-$(C_1-C_6)$alkylene-carbonyl, heteroaryl-carbonyl, heteroaryl-$(C_1-C_6)$alkylene-carbonyl, acyl, or amino; or $R^a$ and $R^b$ together with the carbon atom to which they are attached form a three, four, five or six membered cycloalkyl ring that optionally includes an additional heteroatom selected from O, N and S;

$R^{ca}$ and $R^{cb}$ are independently hydrogen, $(C_1-C_8)$alkyl or $(C_1-C_6)$alkoxy-$(C_1-C_6)$alkylene;

Y is $NO_2$, acyl, cyano, $(C_1-C_6)$alkylsulfonyl, $SO_2OR'$, $PO(OR')_2$, or $CF_3$, most preferably Y is cyano; and R' is hydrogen or $(C_1-C_8)$alkyl;

comprising reacting a compound of formula ($II_a$):

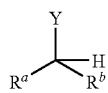

with an alkylating agent such as 1-halo-$CH(R^{ca})(R^{cb})$ or a sulfonate ester of $(R^{ca})(R^{cb})CH$—OH, wherein $R^{ca}$ and $R^{cb}$ are as defined above, preferably in the presence of a secondary amine, and a Grignard reagent, such as $(C_1-C_6)$alkyl-magnesium-halide, phenyl-magnesium-halide, heteroaryl-magnesium-halide or cycloakyl-magnesium-halide."

A. Definitions

Unless otherwise stated, the following terms used in the specification and claims have the meanings given below. All references cited herein are hereby incorporated by reference in their entirety.

The term "halo" means fluoro, chloro, bromo or iodo, preferably chloro or bromo. "alkali metal" or "alkali" refers to lithium, sodium, potassium, rubidium and caesium. Preferable alkali metal is lithium or sodium. Of these, sodium is most preferred.

"$(C_1-C_8)$alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl and heptyl. $(C_1-C_6)$alkyl is preferred.

"$(C_1-C_6)$alkylcarbonyl" means a group —C(O)—$R^{aa}$ wherein $R^{aa}$ is $(C_1-C_6)$alkyl as defined herein.

"$(C_1-C_6)$alkoxy" means a moiety of the formula —$OR^{ab}$, wherein $R^{ab}$ is an $(C_1-C_6)$alkyl moiety as defined herein. Examples of alkoxy moieties include, but are not limited to, methoxy, ethoxy, isopropoxy, and the like.

"$(C_1-C_6)$Alkoxy$(C_1-C_6)$alkylene" means a moiety of the formula $R^{ac}$—O—$R^{ad}$—, where $R^{ac}$ is $(C_1-C_6)$alkyl and $R^{ad}$ is $(C_1-C_6)$alkylene as defined herein. Exemplary $(C_1-C_6)$alkoxy$(C_1-C_6)$alkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"$(C_1-C_6)$alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Halo-$(C_1-C_8)$alkyl" refers to an alkyl, as defined above, substituted with one or more halogen atoms, preferably with one to three halogen atoms. More preferred halo-$(C_1-C_8)$alkyl is the chloro- and fluoro-$(C_1-C_8)$alkyl.

"Halo-$(C_1-C_6)$alkoxy" refers to an alkoxy, as defined above, substituted with one or more halogen atoms, preferably with one to three halogen atoms. More preferred halo-$(C_1-C_6)$alkoxy are the chloro- and fluoro-$(C_1-C_8)$alkoxy.

"$(C_3-C_6)$cycloalkyl" refers to a single saturated carbocyclic ring of thee to six ring carbons, such as cyclopropyl, cyclobutyl, cyclopentyl and cyclohexyl. Cycloalkyl may optionally be substituted with one or more substituents, preferably one, two or three, substituents. Preferably, cycloalkyl substituent is selected from the group consisting of $(C_1-C_6)$alkyl, hydroxy, $(C_1-C_6)$alkoxy, halo$(C_1-C_6)$alkyl, halo$(C_1-C_6)$alkoxy, halo, amino, mono- and di$(C_1-C_6)$alkylamino, hetero$(C_1-C_6)$alkyl, acyl, aryl and heteroaryl.

"$(C_3-C_6)$Cycloalkyl$(C_1-C_6)$alkylene" refers to a moiety of the formula $R^{ae}$—$R^{af}$—, where $R^{ae}$ is $(C_3-C_6)$cycloalkyl and $R^{af}$ is $(C_1-C_6)$alkylene as defined herein.

"Secondary amine" refers to an amine of formula $HNR^2R^3$ wherein $R^2$ and $R^3$ may be the same or different and are independently selected from $(C_1-C_6)$alkyl or $(C_3-C_6)$cycloalkyl, or $R^2$ and $R^3$ taken together with the nitrogen atom to which they are attached, form a $(C_4-C_8)$heterocycloalkane optionally containing an additional heteroatom selected from O or N.

Representative examples include, but are not limited to, piperidine, 4-methyl-piperidine, piperazine, pyrrolidine, morpholine, dimethylamine, diethylamine, diisopropylamine, dicyclohexylamine, ethylmethylamine, ethylpropylamine and methylpropylamine. Preferably, the secondary amine is chosen from diethylamine, diisopropylamine, dicyclohexylamine, ethylmethylamine, ethylpropylamine, methylpropylamine and morpholine. The more preferred secondary amine is diethylamine or diisopropylamine, most preferred diethylamine.

"$(C_4-C_8)$heterocycloalkane" refers to a saturated non-aromatic cyclic compound of 4 to 8 ring atoms in which one or two ring atoms are heteroatoms selected from N or O, and the heterocycloalkane may be optionally substituted with one or more $(C_1-C_3)$alkyl, preferably one $(C_1-C_3)$alkyl.

"Acyl" means a group of the formula —C(O)—$R^{ag}$, —C(O)—O$R^{ag}$, —C(O)—OC(O)$R^{ag}$ or —C(O)—N$R^{ag}R^{ah}$ wherein $R^{ag}$ is hydrogen, $(C_1-C_6)$alkyl, halo$(C_1-C_6)$alkyl, heteroalkyl or amino as defined herein, and $R^{ah}$ is hydrogen or $(C_1-C_6)$alkyl as defined herein.

"Amino" means a group —N$R^{ba}R^{bb}$ wherein $R^{ba}$ and $R^{bb}$ each independently is hydrogen or $(C_1-C_6)$alkyl.

"Aryl" means a monovalent monocyclic or bicyclic aromatic hydrocarbon moiety which is optionally substituted with one or more, preferably one, two or three, substituents, each of which is preferably selected from the group consisting of $(C_1-C_6)$alkyl, hydroxy, $(C_1-C_6)$alkoxy, halo$(C_1-C_6)$alkyl, halo$(C_1-C_6)$alkoxy, halo, nitro, cyano, amino, mono- and di$(C_1-C_6)$alkylamino, methylenedioxy, ethylenedioxy, acyl, hetero$(C_1-C_6)$alkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula —$R^{bc}$—$R^{bd}$ where $R^{bd}$ is aryl and $R^{bc}$ is $(C_1-C_6)$alkylene as defined herein.

"Arylcarbonyl" means a group —C(O)_$R^{be}$ wherein $R^{be}$ is aryl as defined herein.

"Aryl-$(C_1-C_6)$alkylene-carbonyl" means a group —C(O)—$R^{bf}$—$R^{bg}$ wherein $R^{bf}$ is $(C_1-C_6)$alkylene and $R^{bf}$ is aryl as defined herein.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from $(C_1-C_6)$alkyl, halo$(C_1-C_6)$alkyl, hydroxy, $(C_1-C_6)$alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. "Heteroaryl$(C_1-C_6)$alkylene" and "heteroaralkyl" refers to a moiety of the formula $Ar^z$-$R^y$—, where $Ar^z$ is heteroaryl and $R^y$ is $(C_1-C_6)$alkylene as defined herein.

"Heteroarylcarbonyl" means a group —C(O)—$R^{bh}$ wherein $R^{bh}$ is heteroaryl as defined herein.

"Heteroaryl-$(C_1-C_6)$alkylene-carbonyl" means a group —C(O)—$R^{bf}$—$R^{bg}$ wherein $R^{bf}$ is $(C_1-C_6)$alkylene and $R^{bf}$ is heteroaryl as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from $(C_1-C_6)$alkyl, halo$(C_1-C_6)$alkyl, hydroxy$(C_1-C_6)$alkyl, halo, nitro, cyano, cyano$(C_1-C_6)$alkyl, hydroxy, $(C_1-C_6)$alkoxy, amino, mono- and di$(C_1-C_6)$alkylamino, aralkyl, —$(X)_n$—C(O)$R^e$ (where X is O or N$R^f$, n is 0 or 1, $R^e$ is hydrogen, $(C_1-C_6)$alkyl, halo$(C_1-C_6)$alkyl, hydroxy (when n is 0), $(C_1-C_6)$alkoxy, amino, mono- and di$(C_1-C_6)$alkylamino, or optionally substituted phenyl, and $R^f$ is H or $(C_1-C_6)$alkyl), —$(C_1-C_6)$alkylene-C(O)$R^g$ (where $R^g$ is $(C_1-C_6)$alkyl, —O$R^h$ or N$R^iR^j$ and $R^h$ is hydrogen, $(C_1-C_6)$alkyl or halo$(C_1-C_6)$alkyl, and $R^i$ and $R^j$ are independently hydrogen or $(C_1-C_6)$alkyl), and —$S(O)_nR^k$ (where n is an integer from 0 to 2) such that when n is 0, $R^k$ is hydrogen, $(C_1-C_6)$alkyl, $(C_3-C_6)$cycloalkyl, or $(C_3-C_6)$cycloalkyl$(C_1-C_6)$alkyl, and when n is 1 or 2, $R^k$ is $(C_1-C_6)$alkyl, $(C_3-C_6)$cycloalkyl, $(C_3-C_6)$cycloalkyl$(C_1-C_6)$alkyl, amino, acylamino, mono$(C_1-C_6)$alkylamino, or di$(C_1-C_6)$alkylamino. A particularly preferred group of heterocyclyl substituents include $(C_1-C_6)$alkyl, halo$(C_1-C_6)$alkyl, hydroxy $(C_1-C_6)$alkyl, halo, hydroxy, $(C_1-C_6)$alkoxy, amino, mono- and di$(C_1-C_6)$alkylamino, aralkyl, and —$S(O)_nR^k$. In particular, the term heterocyclyl includes, but is not limited to, tetrahydrofuranyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Hetero$(C_1-C_8)$alkyl" means an alkyl moiety as defined herein wherein one or more, preferably one, two or three, hydrogen atoms have been replaced with a substituent independently selected from the group consisting of —O$R^{a'}$, —N$R^{b'}R^{c'}$ and —$S(O)_nR^{d'}$ (where n is an integer from 0 to 2), with the understanding that the point of attachment of the heteroalkyl moiety is through a carbon atom, wherein $R^{a'}$ is hydrogen, acyl, $(C_1-C_6)$alkoxycarbonyl, $(C_1-C_6)$alkyl, hydroxy$(C_1-C_6)$alkyl, $(C_1-C_6)$alkoxy$(C_1-C_6)$alkyl, $(C_1-C_6)$alkylsulfonyl, aminocarbonyl, aminosulfonylamino, $(C_3-C_6)$cycloalkyl, or $(C_3-C_6)$cycloalkyl$(C_1-C_6)$alkyl; $R^{b'}$ and $R^{c'}$ are independently of each other hydrogen, acyl, $(C_1-C_6)$alkoxycarbonyl, aminocarbonyl, aminocarbonyl, aminosulfonylamino, hydroxy$(C_1-C_6)$alkyl, $(C_1-C_6)$alkoxy$(C_1-C_6)$alkyl, $(C_1-C_6)$alkylsulfonyl, $(C_3-C_6)$cycloalkyl, $(C_3-C_6)$cycloalkyl $(C_1-C_6)$alkyl, $(C_1-C_6)$alkylsulfonyl, aminosulfonyl, mono- or di-$(C_1-C_6)$alkylaminosulfonyl, amino$(C_1-C_6)$alkyl, mono- or di-$(C_1-C_6)$alkylaminoalkyl, hydroxy$(C_1-C_6)$alkyl, $(C_1-C_6)$alkoxy$(C_1-C_6)$alkyl, hydroxy$(C_1-C_6)$alkylsulfonyl or $(C_1-C_6)$alkoxy$(C_1-C_6)$alkylsulfonyl; and when n is 0, $R^{d'}$ is hydrogen, $(C_1-C_6)$alkyl, $(C_3-C_6)$cycloalkyl, $(C_3-C_6)$cycloalkyl$(C_1-C_6)$alkyl, or aryl, and when n is 1 or 2, $R^{d'}$ is $(C_1-C_6)$alkyl, $(C_3-C_6)$cycloalkyl, $(C_3-C_6)$cycloalkyl$(C_1-C_6)$ alkyl, hydroxy$(C_1-C_6)$alkyl, $(C_1-C_6)$alkoxy$(C_1-C_6)$alkyl, $(C_1-C_6)$alkylamino, aminocarbonyl, aminosulfonylamino, $(C_1-C_6)$alkylsulfonyl, amino, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Alkylsulfonyl" means a moiety of the formula —SO$_2$R$^{bi}$ wherein R$^{bi}$ is (C$_1$-C$_6$)alkyl.

"Nitrosylating agent" comprises nitrosylsulfuric acid, sodium nitrite or a mixture thereof. Most preferably, the nirtosylating agent is nitrosylsulfuric acid.

"Sulfonate ester" of R$^1$CH$_2$—OH" or (R$^{ca}$)(R$^{cb}$)CH—OH refers to a substituted or an unsubstituted phenyl-sulfonate, an unsubstituted naphthalene-sulfonate or a (C$_1$-C$_6$)alkylsulfonate ester derivative of R$^1$CH$_2$—OH or (R$^{ca}$)(R$^{cb}$)CH—OH, respectively, wherein substituted phenyl and the (C$_1$-C$_6$) alkyl chain, R$^1$, R$^{ca}$, R$^{cb}$ are as defined herein. Representative examples include, but are not limited to, benzenesulfonic acid 2-ethyl-butyl ester, 1-naphthalenesulfonic acid 2-ethyl-butyl ester, 2-naphthalenesulfonic acid 2-ethyl-butyl ester, toluene-4-sulfonic acid 2-ethyl-butyl ester, 4-nitro-benzenesulfonic acid 2-ethyl-butyl ester, 2,4,6-trimethyl-benzenesulfonic acid 2-ethyl-butyl ester, ethanesulfonic acid 2-ethyl-butyl ester, methanesulfonic acid 2-ethyl-butyl ester and butanesulfonic acid 2-ethyl-butyl ester.

"Strong acid" refers to an acid that dissociates completely in an aqueous solution with a pH≦2. The strong acids include, but are not limited to: sulphuric acid (H$_2$SO$_4$), hydrohalogenic acid (i.e. HX" wherein X" is I, Br, Cl or F), nitric acid (HNO$_3$), phosphoric acid (H$_3$PO$_4$) and combinations thereof. Preferably, the strong acid is H$_2$SO$_4$ or hydrohalogenic acid, wherein X" is Br or Cl. Most preferably, the strong acid is H$_2$SO$_4$. Preferably the concentration of H$_2$SO$_4$ in water is in the range of 75% to 90%, more preferably 78 to 83%, most preferably 82.5%. "aqueous base" refers to a solution comprising a base and water. Numerous bases which readily dissolve in water are known in the art, such as NaOH, KOH, Ca(OH)$_2$, Mg(OH)$_2$, preferably NaOH or KOH. More preferably the aqueous base has a pH of 12 to 14.

DETAILED DESCRIPTION OF THE INVENTION

The present invention generally provides a process for the preparation of compound of formula I$_a$:

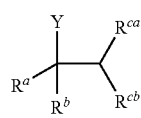

wherein,
R$^a$ is hydrogen, (C$_1$-C$_8$)alkyl, halo-(C$_1$-C$_8$)alkyl, (C$_1$-C$_6$) alkoxy, (C$_1$-C$_6$)alkoxy-(C$_1$-C$_6$)alkylene, hetero-(C$_1$-C$_8$) alkyl, (C$_3$-C$_6$)cycloalkyl, (C$_3$-C$_6$)cycloalkyl-(C$_1$-C$_6$)alkylene, aryl, aralkyl, heteroaryl, heteroaryl-(C$_1$-C$_6$)alkylene, (C$_1$-C$_6$)alkyl-carbonyl, aryl-carbonyl, aryl-(C$_1$-C$_6$)alkylene-carbonyl, heteroaryl-carbonyl, heteoaryl-(C$_1$-C$_6$) alkylene-carbonyl, acyl, amino; NO$_2$, -cyano, SO$_2$OR', or PO(OR')$_2$;
R$_b$ is hydrogen, (C$_1$-C$_8$)alkyl, halo-(C$_1$-C$_8$)alkyl, (C$_1$-C$_6$) alkoxy, (C$_1$-C$_6$)alkoxy-(C$_1$-C$_6$)alkylene, hetero-(C$_1$-C$_8$) alkyl, (C$_3$-C$_6$)cycloalkyl, (C$_3$-C$_6$)cycloalkyl-(C$_1$-C$_6$)alkylene, aryl, aralkyl, heteroaryl, heteroaryl-(C$_1$-C$_6$)alkylene, (C$_1$-C$_6$)alkyl-carbonyl, aryl-carbonyl, aryl-(C$_1$-C$_6$)alkylene-carbonyl, heteroaryl-carbonyl, heteoaryl-(C$_1$-C$_6$) alkylene-carbonyl, acyl, or amino;

or

R$^a$ and R$^b$ together with the carbon atom to which they are attached form a three, four, five or six membered cycloalkyl ring that optionally includes an additional heteroatom selected from O, N and S;

R$^{ca}$ and R$^{cb}$ are independently hydrogen, (C$_1$-C$_8$)alkyl or (C$_1$-C$_6$)alkoxy-(C$_1$-C$_6$)alkylene;

Y is —NO$_2$, -acyl, -cyano, —(C$_1$-C$_6$)alkylsulfonyl, —SO$_2$OR', —PO(OR')$_2$, or —CF$_3$, most preferably Y is cyano; and R' is hydrogen or (C$_1$-C$_8$)alkyl;

comprising reacting a compound of formula (II$_a$):

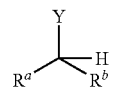

with an alkylating agent such as 1-halo-CH(R$^{ca}$)(R$^{cb}$) or a sulfonate ester of (R$^{ca}$)(R$^{cb}$)CH—OH, wherein R$^{ca}$ and R$^{cb}$ are as defined above, preferably in the presence of a secondary amine, and a Grignard reagent, such as (C$_1$-C$_6$)alkyl-magnesium-halide, phenyl-magnesium-halide, heteroaryl-magnesium-halide or cycloakyl-magnesium-halide."

In a second embodiment, the present invention provides a process for the preparation of the compound of a cyclohexanecarbonitrile derivative of formula (I):

In a second embodiment, the present invention provides a process for the preparation of the compound of a cyclohexanecarbonitrile derivative of formula (I):

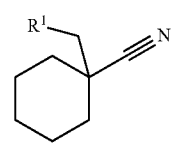

wherein R$^1$ is (C$_1$-C$_8$)alkyl, preferably pent-3-yl,
comprising reacting cyclohexanecarbonitrile of formula (II)

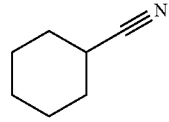

with an alkylating agent such as a 1-halo-CH$_2$R$^1$, preferably 1-halo-2-ethylbutane, or a sulfonate ester of R$^1$CH$_2$—OH, preferably of 2-ethyl-1-butanol, wherein R$^1$ is as defined above, and a Grignard reagent, such as (C$_1$-C$_6$)alkyl-magnesium-halide, phenyl-magnesium-halide, heteroaryl-magnesium-halide or (C$_3$-C$_6$)cycloakyl-magnesium-halide.

Preferably the above mentioned coupling reaction is carried out in the presence of a secondary amine.

Preferably, the Grignard reagent is added to the cyclohexanecarbonitrile, more preferably in the presence of a secondary amine, followed by the addition of an alkylating agent, as defined above.

Preferably the above mentioned coupling reaction is followed by a mineral acid quenching, such as hydrofluoric acid, hydrochloric acid, boric acid, acetic acid, formic acid, nitric acid, phosphoric acid or sulfuric acid, most preferably by hydrochloric acid.

In another embodiment the present invention further provides a process for the preparation of a cyclohexanecarboxylic acid derivative of formula (III):

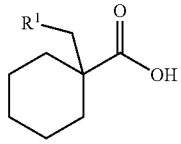

(III)

wherein $R^1$ is as defined previously, comprising:
a) hydrolysing a cyclohexanecarbonitrile derivative of formula (I):

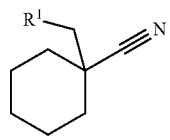

(I)

with $H_2O$ in the presence of a strong acid, or with an aqueous base, to obtain a cyclohexanecarboxylic acid amide derivative of formula (IV);

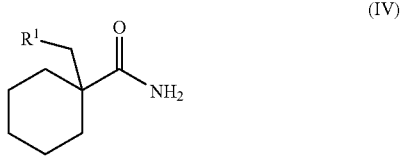

(IV)

b) reacting the said cyclohexanecarboxylic acid amide derivative with a nitrosylating agent, to obtain the compound of formula (III).

The compound of formula (III) may be used as intermediate in the synthesis of valuable pharmaceutical compounds. For example 1-(2-ethyl-butyl)-cyclohexanecarboxylic acid may be used in the synthesis of the ones as described in EP 1,020,439.

Accordingly, in another embodiment the present invention provides a process comprising the synthetic steps represented in the following scheme 1:

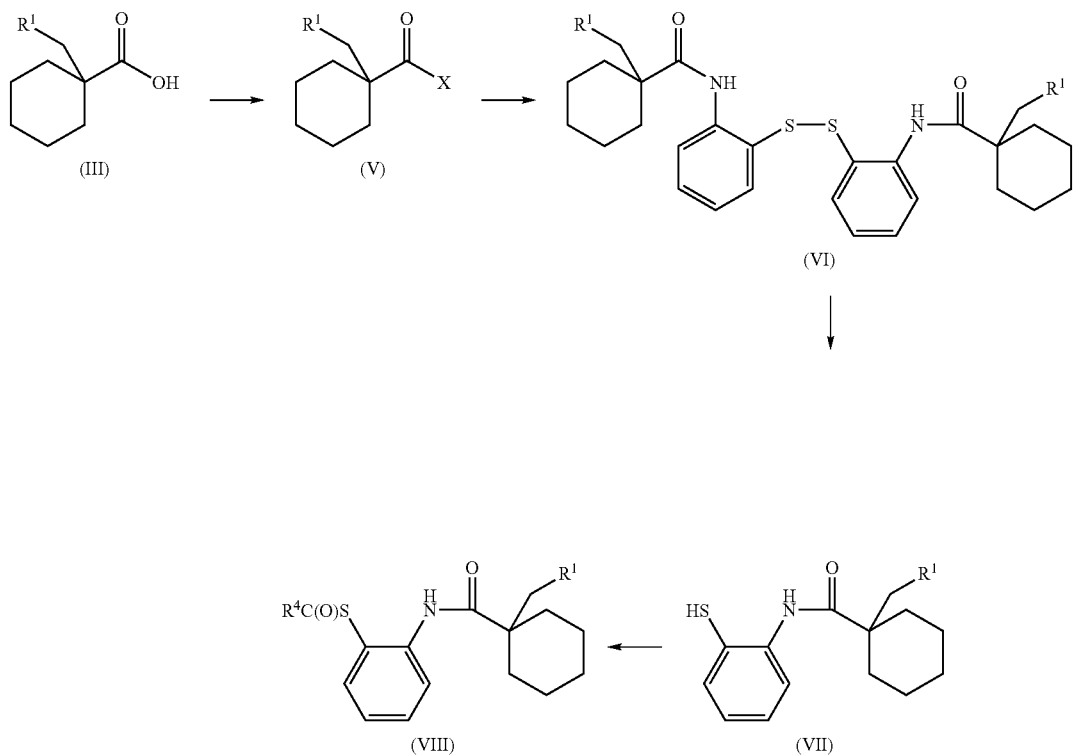

Scheme 1.

wherein X is I, Br, Cl or F, $R^1$ is as defined above and $R^4$ is $(C_1-C_8)$alkyl. In particular, the process comprises reacting a cyclohexanecarboxylic acid derivative of formula (III) with a halogenating agent, such as $PX_3$, $PX_5$, $SOX_2$ or NCX, to obtain the acyl halide of formula (V). The halogenating step is preferably carried out in the presence of tri-$(C_1-C_5)$alkylamine. Furthermore, the process comprises reacting acyl halide with bis(2-aminophenyl)disulfide to acylate the amino groups of the bis(2-aminophenyl)disulfide, reducing the amino-acylated disulfide product with a reducing agent such as triphenylphosphine, zinc or sodium borohydride to yield the thiol product, and acylating the thiol group in the thiol product with $R^4C(O)X'$, wherein X' is I, Br, Cl or F.

The additional steps may be performed, e.g., according to the procedures described in Shinkai et al., J. Med. Chem. 43:3566-3572 (2000) or WO 2007/051714.

Preferably the halogenating agent is chosen from thionyl chloride, phosphorus pentachloride, oxalyl chloride, phosphorus tribromide and cyanuric fluoride, most preferably thionyl chloride.

The acyl halide of formula (V) wherein X is Cl is most preferred.

In the thiol acylation step, preferably the acylating agent is $R^4C(O)X'$, wherein X' is Cl. Most preferably $R^4$ is isopropyl.

In yet another embodiment, the present invention provides a process for the preparation of a cyclohexanecarboxylic acid derivative of formula (III);

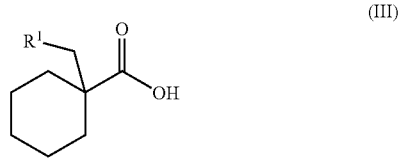

wherein $R^1$ is as defined above, comprising:
a) hydrolysing a cyclohexanecarbonitrile derivative of formula (I):

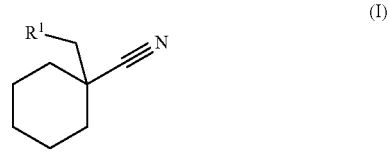

with water in the presence of a strong acid or with an aqueous base to obtain a cyclohexanecarboxylic acid amide derivative of formula (IV);

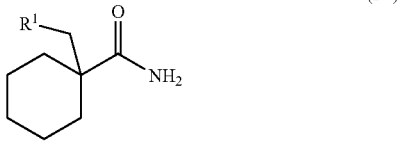

b) reacting the said cyclohexanecarboxylic acid amide derivative (IV) with a nitrosylating agent to obtain the compound of formula (III);
c) solution extracting the compound of formula (III), preferably out of an organic solvent by adjusting the solution to a basic pH, preferably of pH of 9 to 14, more preferably to pH of 11 to 13.5, most preferably to pH of 12.5 to 13, by addition of a basic aqueous solution, then separating phases, discarding the organic phase, adding fresh organic phase, adjusting the aqueous phase to a pH of 1 to 10, preferably to a pH of 3 to 8, most preferably to a pH of 6 to 7, by acidifying the solution, preferably by addition of a mineral acid, such as hydrofluoric acid, hydrochloric acid, boric acid, nitric acid, phosphoric acid or sulfuric acid, or an organic acid such as formic acid or acetic acid, more preferably the acid is a mineral acid, most preferably hydrochloric acid and thereby extracting the compound of formula (III) into the organic phase.

Preferably after the hydrolysis of compound (I), steps a) and b), the biphasic mixture is separated, the water solution is back extracted with an organic solvent, and $H_2O$ is added to the combined organic phases of the reaction mixture. Then, the pH of the biphasic solution is adjusted to 10 to 14, preferably to a pH of 11 to 13.5 by addition of a basic aqueous solution as defined herein, preferably over a period of 10 min. The organic phase is discarded and a water saturated solution of NaCl and an organic solvent, as defined herein, more preferably toluene, is added to the water phase, more preferably the organic phase is discarded and water and an organic solvent is added to the water phase. After this, the pH of the mixture is adjusted to a pH of 6 to 7 by addition of a mineral acid as previously defined. The water phase is discarded and the organic layer is concentrated.

Unless otherwise stated, organic solvent referred herein comprises ether like solvent (e.g. tetrahydrofuran, methyltetrahydrofuran, diisopropyl ether, t-butylmethyl ether or dibutyl ether, ethyl acetate, butyl acetate), alcohol solvent (e.g. methanol or ethanol), aliphatic hydrocarbon solvent (e.g. hexane, heptane or pentane), saturated alicyclic hydrocarbon solvent (e.g. cyclohexane or cyclopentane) or aromatic solvent (e.g. toluene or t-butyl-benzene) In a further embodiment, the present invention provides processes as described above wherein nitrosylating agent is generated in situ e.g. mixing $H_2SO_4$ and nitrous acid ($HNO_2$) or $H2SO_3/HNO_3$ or $N_2O_3/H_2SO_4$ or $HNO_3/SO_2$ to obtain nitrosulfuric acid ($NOHSO_4$).

In a further embodiment, the present invention provides a process for the preparation of the compound of formula (III), comprising the preparation of a cyclohexanecarbonitrile derivative of formula (I) followed by the hydrolysis steps as described above and in the following scheme 2, wherein $R^1$ is as defined above.

Scheme 2:

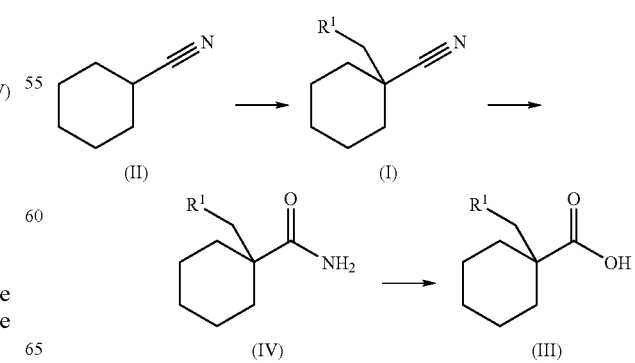

Within the processes defined above, preferably the halide of Grignard reagent is chosen from chloride, bromide and iodide, more preferably chloride or bromide, most preferably chloride.

The preferred alkyl of the Grignard reagent is ($C_1$-$C_3$) alkyl, more preferably methyl. The most preferred Grignard reagent is methylmagnesiumchloride.

The preferred alkylating agent is 1-halo-2-ethylbutane, most preferably 1-bromo-2-ethylbutane.

Preferably the alkylation is performed with catalytic amount of secondary amine, such as 0.01 to 0.5 equivalent of secondary amine with respect to cyclohexylcarbonitrile, most preferably 0.20 eq. The dosing time of the methylmagnesiumchloride, is preferably 0.5 to 4 h, most preferably 1.5 h. This addition is preferably carried out at room temperature. The 2-ethylbutylbromide dosing time is preferably 0.5 to 2 h, most preferably 1 h. The 2-ethylbutylbromide is preferably added at temperature of 40 to 50 C.

A nonprotic organic solvent is the preferred solvent during the alkylation, such as tetrahydrofuran, alone or in combination with another nonprotic solvent, e.g. from the group of the apolar solvents hexane, heptane, methyl tetrahydrofurane, toluene and t-butyl-benzene, more preferably hexane, heptane, toluene and t-butyl-benzene. Most preferably the nonprotic solvent is tetrahydrofuran.

Preferably the hydrolysing agent of the cyclohexanecarbonitrile derivative of formula (I) is a strong acid. The most preferred strong acid for step a) is $H_2SO_4$. The hydrolysis step is either carried out by dosing compound of formula (I) to $H_2SO_4$ at temperature of 80° C. to 120° C. or both compound of formula (I) and $H_2SO_4$ are heated as a mixture to a temperature of 80° C. to 120° C. More preferably the temperature in both modes of addition is 95 to 110° C., most preferably 105 to 110° C. 1.5 to 4 equivalents of $H_2SO_4$ with respect to compound of formula (I) is preferably used. More preferably 1.9 to 3.6 equivalents are used. Most preferably 2 equivalents are used. The hydrolysis is carried out with excess $H_2O$, preferably 5 to 25 eq. of $H_2O$ with respect to the compound of formula (I), more preferably 10 to 20 eq. Most preferably, 14 to 16 eq. of $H_2O$ is used with respect to the compound of formula (I).

For the hydrolysis of the amide of formula (IV), preferably 1.1 to 1.4 equivalents of nitrosylsulfuric acid is used, most preferably 1.2 to 1.4 equivalent. Either nitrosylsulfuric acid is added first and followed by $H_2O$ or the $H_2O$ is first added and followed by addition of nitrosylsulfuric acid. The second addition mode is preferred. Preferably, the dosing temperature is at 20 to 65° C., most preferably 60 to 65° C.

According to the present invention the "basic aqueous solution" for the extraction step (c) is preferably chosen from inorganic bases or organic bases, a mixture thereof, or from commonly known buffering solutions of suitable pH. The preferred inorganic base is an alkali base, such as alkali carbonate, alkali bicarbonate, alkali borate, alkali phosphate, alkali-hydroxide. A more preferred basic aqueous solution is chosen from solution of potassium bicarbonate, sodium bicarbonate, potassium carbonate, sodium carbonate, sodium borate, sodium hydroxide, or a mixture thereof. The most preferred basic aqueous solution is a solution of sodium bicarbonate, sodium hydroxide or a mixture thereof.

In a further embodiment the present invention provides a process for the preparation of [2-([[1-(2-ethylbutyl)-cyclohexyl]-carbonyl]amino)phenyl]2-methylpropanethioate comprising the formation of a compound of formula (I) obtained by any of the processes and conditions mentioned previously.

The starting materials and reagents, which do not have their synthetic route explicitly disclosed herein, are generally available from commercial sources or are readily prepared using methods well known to the person skilled in the art. For instance, compound of formula (II) is commercially available or can be prepared by procedures known to the skilled person.

A compound of formula (IV), wherein $R^1$ is pent-3-yl, is new. Accordingly, a further embodiment the present invention provides a compound of formula (IV')

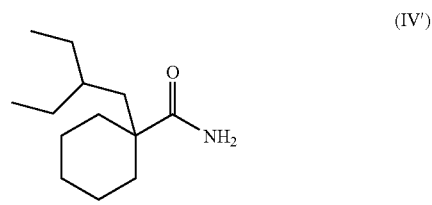

The methods of the present invention may be carried out as semi-continuous or continuous processes, more preferably as continuous processes.

In the case of a continuous conduct of the process for the preparation of the compound of a cyclohexanecarbonitrile derivative of formula (I), a solution ($S^1$) of Grignard reagent (most preferably methylmagnesiumchloride) and secondary amine (most preferably diethylamine), and a solution ($S^2$) of a cyclohexanecarbonitrile are continuously added into a reaction vessel while preferably being mixed. Then the mixture from the deprotonation and a solution ($S^3$) of an alkylating agent (most preferably 2-ethylbutylbromide) were added continuously to a second reaction vessel while preferably being mixed. Preferably, the reaction mixture is then treated with HCl, the collected organic phase are washed with water, and concentrated under reduced pressure to yield cyclohexanecarbonitrile derivative of formula (I). In the continuous process, the preferred reaction vessels are microreactors consisting of mixing and reaction chambers.

Preferably the speeds of addition of solution ($S^1$) and solution ($S^2$) are between 2.2 and 3.1 mmol/min (most preferably 2.64 mmol/min) and between 1.9 and 2.8 mmol/min (more preferably 2.33 mmol/min), respectively. Preferably the contacting time of solution ($S^1$) and ($S^2$) is less than 60 sec (more preferably less than 30 sec, most preferably 12 sec). Preferably the speeds of addition of solution $S^3$ is between 2.1 and 3.0 mol/min, more preferably 2.58 mmol/min and preferably the contacting time is less than 20 min, more preferably is 6 min.

The following examples are provided for the purpose of further illustration and are not intended to limit the scope of the claimed invention.

The following abbreviations and definitions are used: br (broad); BuLi (butyllithium); $CDCl_3$ (deuterated chloroform); eq. (equivalent); g (gram); GC (gas chromatography); h (hour); HCl (hydrochloric acid); $H_2O$ (water); HPLC (High-Performance Liquid Chromatography); ISP (Isotopic Spin Population); KOH (Potassium Hydroxide); LDA (Lithium Diisopropylamide); M (Molar); m (multiplet); MS (Mass Spectroscopy); mL (milliliter); NaOH (Sodium hydroxide); NMR (nuclear magnetic resonance); s (singlet); sec (second); t (triplet); THF (tetrahydrofuran).

EXAMPLE 1

1-(2-Ethyl-butyl)-cyclohexanecarboxylic acid 1.1 1-(2-Ethyl-butyl)-cyclohexylcarbonitrile A solution of 11.0 g (100 mmol) cyclohexylcarbonitrile, 1.46 g (20 mmol) diethylamine and 50.0 ml THF were dosed within 90 minutes with a solution of methylmagnesiumchloride (3M, 112 mmol) in THF at 20-25° C. After completed dosage, the solution was heated to 45° C. and dosed within 60 minutes with 16.7 g (101 mmol) 2-ethylbutylbromide at a rate that the internal temperature was kept between 45-50° C. After additional stirring at 45-50° C. for 60 minutes, the reaction mixture was cooled down to 20-25° C. and treated with 20 ml Heptane, cooled to 0° C. and treated with 55.0 ml HCl (1N) within 60 minutes keeping the internal temperature between 25-30° C. The mixture was stirred for 30 minutes. After that time the phases were separated. The collected organic phase was washed with 75 ml water, concentrated under reduced pressure (190 mbar) at 50° C. and dried in vacuo (15 mbar) at 80° C. yielding 19.0 g of 1-(2-ethyl-butyl)-cyclohexylcarbonitrile with an HPLC assay of 96-98% (yield 97.6%).

1.2 1-(2-Ethyl-butyl)-cyclohexanecarboxylic acid 12.66 g (106.5 mmol) $H_2SO_4$ (82.5%) were heated to 109° C. and dosed with 6.38 g (30.0 mmol) 1-(2-ethyl-butyl)-cyclohexylcarbonitrile continuously within 1 h. After completed dosage, the reaction mixture was stirred for 1 h at 103-104° C. After that time, the reaction mixture was cooled down to 40° C. and treated with 30.0 ml heptane. 10.0 ml $H_2O$ were added within 5 minutes and after completed addition, the mixture was stirred for further 30 minutes at 40° C. After that time 13.34 g (42.0 mmol) nitrosylsulfuric acid were dosed continuously to the mixture within 1 h at a rate that the internal temperature was kept between 60-65° C. After additional stirring at 60-62° C., the reaction mixture was cooled down to 20-25° C. After phase separation, the aqueous phase was extracted with 30.0 ml heptane and the collected organic phases were washed with 30.0 ml $H_2O$. Evaporation of the organic phase in vacuo (110 mbar) at 50° C. gave 6.20 g of 1-(2-ethyl-butyl)-cyclohexanecarboxylic acid as a slightly yellowish oil with an HPLC assay of 95.5% m/m (yield 92.2%).

EXAMPLE 2

1-(2-Ethyl-butyl)-cyclohexanecarboxylic acid amide 21.3 g (110.2 mmol) 1-(2-ethyl-butyl)cyclohexylcarbonitrile and 46.5 g (391.2 mmol) $H_2SO_4$ (82.5%) were mixed, heated to 100° C. and stirred for 3 h at 100° C. After that time, the reaction mixture was cooled down to 20° C., quenched with 50.0 mL water and the pH was adjusted to pH=7-8 by addition of 86.0 ml of NaOH 28%. 50 mL of methylene-chloride was added and after phase separation, the aqueous phase was extracted again with 50.0 ml methylene-chloride. The organic phases were combined and concentrated in vacuo. The residue was crystallized from n-hexanes. 16.5 g of 1-(2-ethyl-butyl)-cyclohexanecarboxylic acid amide were obtained as colorless crystals with an HPLC assay of 100.0% m/m (yield 70.8%).

IR; 3426, 2923, 2855, 1632, 1459, 1379, 511 cm−1

$H^1$NMR (400 MHz, $CDCl_3$, ppm): 5.63 (br.s., 2H), 1.93 (m, 2H), 1.64-1.53 (m, 3H), 1.49-1.38 (m, 4H), 1.36-1.22 (m, 8H), 0.81 (t, 6H)

MS: m/e 212 (M+1)$^+$

Anal. Calc. for $C_{13}H_{25}NO$: C, 73.88; H, 11.92; N, 6.63. Found: C, 73.77; H, 11.66; N, 6.61

EXAMPLE 3

1-(2-Ethyl-butyl)-cyclohexanecarboxylic acid

To a continuously stirred solution of 23.8 g (200 mmol) of $H_2SO_4$ (82.5% solution in water) heated to 105° C.-110° C., was added dropwise, over a period of 60 min, under argon, 20.4 g (100 mmol) of 1-(2-ethyl-butyl)cyclohexylcarbonitrile. Then, the reaction mixture was stirred for a further 2 h at 105° C.-110° C., by GC analysis less than 0.5% of starting nitrile remained in the mixture. Once the reaction mixture was cooled down to 65° C., 100 ml of heptane was added. Then, 26.5 g (1.47 mol) of $H_2O$ was added over a period 5 to 10 min. To the two phases reaction mixture, at 60-65° C., under heavy stirring (800 rpm), over a period of 60 min, was added 44.5 g (140 mmol) of nitrosylsulfuric acid (40% in sulfuric acid), with the help of an infusion pump. The reaction mixture was stirred for a further 30 min at 60-65° C. The reaction mixture was allowed to cool and settle down to room temperature. The aqueous phase was discarded. Then to the organic phase was added 100.0 ml $H_2O$. The pH of the solution was adjusted to 12.5-13 by addition of approximately 38 g of sodium hydroxide (28% solution in water) at 20-30° C. while stirring, over a 10 min period with the help of dropping funnel. Both phases were allowed to separate for 5 min. The organic phase was discarded and 24 g (20 ml) saturated solution of NaCl and 240 ml of toluene were added to the water phase. Over a 10 min period, with the help of dropping funnel, while stirring the pH was adjusted to 6-7 with approximately 26 g HCl (37% solution in water). Both phases were allowed to separate for 5 min. The organic layer was concentrated under reduced pressure at giving 1-(2-ethyl-butyl)-cyclohexanecarboxylic acid, 20.6 g with a GC assay of 98.1% m/m (yield 95%).

EXAMPLE 4

1-(2-Ethyl-butyl)-cyclohexylcarbonitrile

A solution of 8.74 g (80 mmol) cyclohexylcarbonitrile and 40.0 ml THF were dosed within 105 minutes with a solution of methylmagnesiumchloride (3M, 30 mls, 89 mmol) in THF at 20-26° C. After dosing was completed, the solution was heated to 46° C. and dosed within 60 minutes with 15.6 g (94.5 mmol) 2-ethylbutylbromide at a rate that the internal temperature was kept between 45-50° C. After additional stirring at 45-50° C. for 22 hours, the reaction mixture was cooled down to 20-25° C. and treated with 28 ml Heptane, cooled to 0° C. and treated with 45 ml HCl (1N) within 60 minutes keeping the internal temperature between 3-6° C. The temperature was adjusted to 20-26° C. and the mixture was stirred for 30 minutes. After that time the phases were separated. The collected organic phase was washed with water, concentrated under reduced pressure at 50° C. and dried in vacuo at 80° C. yielding 11.19 g of 1-(2-ethyl-butyl)-cyclohexylcarbonitrile with an GC assay of 67.8% (yield 49.0% of title compound and 16% of acetyl cyclohexane).

EXAMPLE 5

1-(2-Ethyl-butyl)-cyclohexanecarboxylic acid

To a continuously stirred solution of 23.8 g (200 mmol) of $H_2SO_4$ (82.5% solution in water) heated to 105° C.-110° C., was added dropwise, over a period of 60 min, under argon, 20.9 g (100 mmol) of 1-(2-ethyl-butyl)cyclohexylcarbonitrile. Then, the reaction mixture was stirred for a further 2 h at 105° C.-110° C., by GC analysis less than 0.5% of starting nitrile remained in the mixture. Once the reaction mixture was cooled down to 65° C., 100 ml of heptane was added. Then, 26.5 g (1.47 mol) of H$_2$O was added over a period 5 to 10 min. To the two phases reaction mixture, at 60-65° C., under heavy stirring (800 rpm), over a period of 60 min, was added 47.7 g (140 mmol) of nitrosylsulfuric acid (40% in sulfuric acid), with the help of an infusion pump. The reaction mixture was stirred for a further 30 min at 60-65° C. The reaction mixture was allowed to cool and settle down to room temperature. The aqueous phase was discarded. Then to the organic phase was added 100.0 ml H$_2$O. The pH of the solution was adjusted to 12.5-13 by addition of approximately 17 g of sodium hydroxide (28% solution in water) at 20-30° C. while stirring, over a 10 min period with the help of dropping funnel. Both phases were allowed to separate for 5 min. The organic phase was discarded and 100 ml of toluene were added to the water phase. Over a 10 min period, with the help of dropping funnel, while stirring the pH was adjusted to 6-7 with approximately 12 g HCl (37% solution in water). Both phases were allowed to separate for 5 min. The organic layer was concentrated under reduced pressure at giving 1-(2-ethyl-butyl)-cyclohexanecarboxylic acid in toluene, 37.0 g with a GC assay of 52.1% m/m (yield 91%).

EXAMPLE 6

1-(2-Ethyl-butyl)-cyclohexylcarbonitrile

EHRFELD's microreactor units were used in the following example. To avoid engassing within the reaction equipment a preparative step was necessary before entering the micro-reaction system. A solution A of 96.05 g methylmagnesium-chloride (3M, 296.8 mmol) in THF was dosed within 30 minutes with a solution of 23.06 g (309.72 mmol) diethylamine in 116.5 ml THF at 20-25° C. After additional stirring at 20-25° C., the reaction mixture was treated with an argon flow for 30 minutes to strip methane.

The solution (A) was continuous dosed with a solution (B) of 28.34 g (258.1 mmol) Cyclohexancarbonitrile in 123.2 ml THF at 20-25° C. in a mixing system, where the reaction takes place. [Solution (A) 2.25 ml/min, solution (B) 1.38 ml/min, residence time 12 seconds]. The mixture from this deprotonation was continuously dosed together with a solution (C) of 47.14 g (283.9 mmol) 2-Ethyl-butyl-bromide in 112 ml THF at 66° C. after a mixing device into a micro reactor. [Solution (C) 1.38 ml/min, residence time 6 minutes].

The reaction mixture (Sample 15 min flow) was cooled down to 20-25° C. and treated with 20.0 ml HCl (1N) within 30 minutes keeping the internal temperature between 25-30° C. The mixture was stirred for 30 minutes. After that time the phases were separated. The collected organic phase was washed with 27 ml water, concentrated under reduced pressure (190 mbar) at 50° C. and dried in vacuo (15 mbar) at 80° C. yielding 5.17 g of 1-(2-ethyl-butyl)-cyclohexylcarbonitrile with an HPLC assay of 83.5% (yield 63.7%).

The invention claimed is:

1. A process for the preparation of a compound of formula (I):

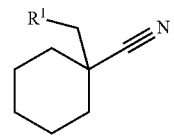

wherein R$^1$ is pentyl-3-yl,
comprising reacting the cyclohexanecarbonitrile of formula (II):

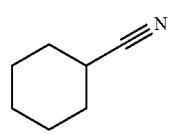

with an alkylating agent and a Grignard reagent, wherein the Grignard reagent is selected from the group consisting of a (C$_1$-C$_6$)alkyl-magnesium-halide, phenyl-magnesium-halide, heteroaryl-magnesium-halide, and cycloalkyl-magnesium-halide.

2. The process of claim 1, wherein the coupling reaction is carried out in the presence of a secondary amine.

3. A process comprising the preparation of a compound of formula (III):

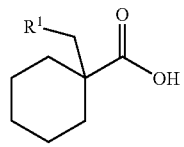

wherein R$^1$ is pentyl-3-yl, comprising:
a) hydrolysing a compound of formula (I) made by the process of claim 1, wherein R$^1$ is pentyl-3-yl:

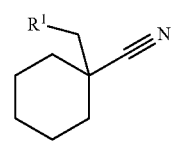

with H$_2$O in the presence of a strong acid, or with an aqueous base, to obtain a compound of formula (IV):

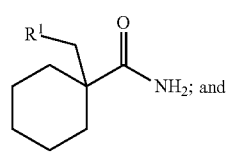

b) reacting the compound of formula (IV) with a nitrosylating agent, to obtain the compound of formula (III).

4. The process of claim 3, further comprising solution extracting the compound of formula (III) by adjusting the solution to a basic pH, then adjusting the aqueous phase to a pH of 1 to 10 by the addition of a mineral acid.

5. The process of claim 3 additionally comprising the preparation of a compound of formula (V):

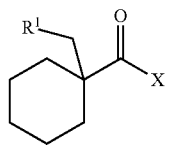

(V)

wherein X is I, Br, Cl or F,
comprising reacting a halogenating agent in the presence of a tri-$(C_1$-$C_5)$alkylamine with a compound of formula (III) as defined in claim 3.

6. The process of claim 5 additionally comprising the preparation of a compound of formula (VI):

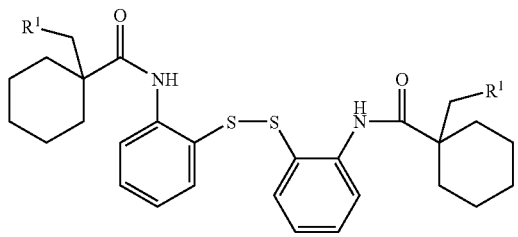

(VI)

wherein $R^1$ is pentyl-3-yl which comprises acylating a compound of formula (VI'):

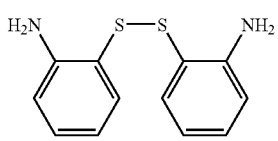

(VI')

with a compound of formula (V) as defined in claim 5 to obtain a compound of formula (VI).

7. The process of claim 6 further comprising reducing the compound of formula (VI) as defined in claim 6 with a reducing agent to obtain a compound of formula (VII):

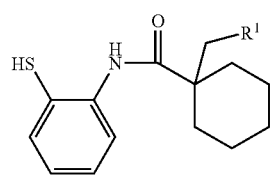

(VII)

wherein $R^1$ is pentyl-3-yl.

8. The process of claim 7 further comprising acylating the compound of formula (VII) with $R^4C(O)X'$, wherein X' is I, Br, Cl or F, to obtain a compound of formula (VIII):

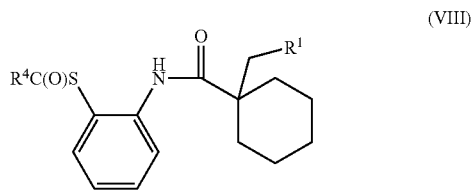

(VIII)

wherein $R^4$ is a $(C_1$-$C_8)$alkyl and $R^1$ is pentyl-3-yl.

9. The process of claim 1, wherein the Grignard reagent is added to the cyclohexanecarbonitrile of formula (II), in the presence of a secondary amine, followed by the addition of the alkylating agent.

10. The process of claim 1, wherein the Grignard reagent is a $(C_1$-$C_6)$alkyl-magnesium-halide.

11. The process of claim 1, wherein the alkylating agent is 1-bromo-2-ethylbutane.

12. The process of claim 9, wherein the Grignard reagent is methylmagnesiumchloride.

13. The process of claim 1, wherein the process is semi-continuous or continuous.

14. A process for the preparation of a compound of formula (I'):

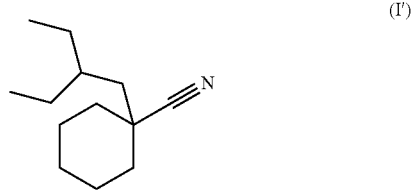

(I')

comprising reacting a cyclohexanecarbonitrile of formula (II):

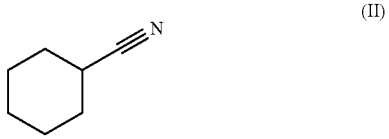

(II)

with an alkylating agent and a Grignard reagent.

15. A compound of formula (IV'):

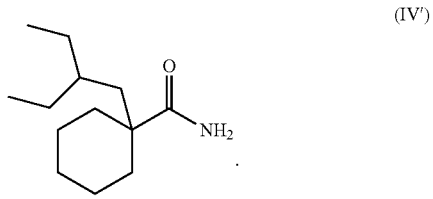

(IV')

* * * * *